United States Patent
Besuner et al.

(10) Patent No.: US 6,270,249 B1
(45) Date of Patent: Aug. 7, 2001

(54) VERTICALLY RECIPROCATING PERFORATED AGITATOR

(76) Inventors: Robert W. Besuner, 26811 Greentree Ave., Madera, CA (US) 93638; David C. Estrich, 310 South St., Sausalito, CA (US) 94965; Reason W. Bradley, P.O. Box 262, Sausalito, CA (US) 94965; Robert G. Ullrich, 6940 Sayre Dr., Oakland, CA (US) 94611

(*) Notice: Subject to any disclaimer, the term of this patent is extended or adjusted under 35 U.S.C. 154(b) by 0 days.

(21) Appl. No.: 09/407,613

(22) Filed: Sep. 28, 1999

Related U.S. Application Data

(60) Provisional application No. 60/102,558, filed on Sep. 30, 1998.

(51) Int. Cl.[7] ............................................. B01F 11/00
(52) U.S. Cl. .............................. 366/332; 366/342; 366/273
(58) Field of Search .................................. 366/332, 333, 366/334, 335, 342, 349, 255, 256, 257, 259, 260, 273, 274, 275

(56) References Cited

U.S. PATENT DOCUMENTS

| | | |
|---|---|---|
| 1,397,766 * 11/1921 | Lidberg . | |
| 2,813,189 * 11/1957 | Lawler | 366/332 |
| 3,873,268 * 3/1975 | McKie, Jr. . | |
| 4,232,972 11/1980 | Levin . | |
| 4,339,241 * 7/1982 | Stocker | 366/273 |
| 4,477,192 10/1984 | Bonney . | |
| 4,732,487 * 3/1988 | Pollard | 366/332 |
| 4,793,714 12/1988 | Gruber . | |
| 5,100,242 3/1992 | Latto . | |
| 5,443,791 8/1995 | Cathcart et al. . | |
| 5,736,100 4/1998 | Miyake et al. . | |
| 5,834,739 11/1998 | Lockwood et al. . | |

OTHER PUBLICATIONS

Author Unknown, Printout of World Wide Web Image and Text from Address–http://www.hypertask.com/mixer.htm, dated Nov. 29, 1998.

* cited by examiner

Primary Examiner—Tony G. Soohoo

(57) ABSTRACT

The present invention comprises a horizontal, perforated agitator element and means to cause the agitator element to reciprocate vertically within a reservoir containing a fluid suspension, solution, or mixture. The perforations in the agitator element are sized and located so that an array of pipette tips may be inserted into the fluid through the moving agitator element without interference.

8 Claims, 2 Drawing Sheets

VERTICALLY RECIPROCATING PERFORATED AGITATOR

CROSS-REFERENCE TO RELATED APPLICATIONS

This application claims the benefit of Provisional Patent Application No. 60/102,558, filed Sep. 30, 1998.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

This invention relates to a device for agitating fluids, specifically for use with automatic pipetting equipment. The invention is particularly useful for agitation of stratified fluids and for maintaining uniformity of solid-fluid suspensions.

Many laboratory processes employ materials requiring agitation or stirring to obtain or maintain desired properties. Such materials may include suspensions of solid particulate matter in a fluid and mixtures of insoluble fluids. When the constituents of the material have different densities, settling can occur. Laboratories frequently use automated pipetting devices to withdraw samples of such materials from a reservoir. These pipetting devices insert an array (usually rectangular) of pipette tips into the reservoir then aspirate samples of the material into the pipette tips for deposit elsewhere. The material in each sample at each withdrawal must have a known and controlled concentration of the constituents of the material. Therefore, it may be necessary to continuously agitate the material.

In the prior art, numerous varied methods for agitation are described. These prior methods have certain disadvantages for use with automated pipetting equipment:

1) Manual agitation, by shaking the reservoir or using a stirring rod, has the disadvantage of requiring human attention and diligence, which may result in spillage, contamination, inconsistent agitation, interference with the automated equipment, or exposure of people to hazardous materials.

2) Circulation using a pump requires fluid inlets and outlets to the reservoir and requires a pump which may be relatively complex and subject to local accumulation of particulate. The pump may thus be subject to dogging or other failure and may require frequent flushing. In addition, the pump system likely has seals and fittings that may leak Also, it may be difficult to avoid "dead spots" within the reservoir where circulation does not occur, allowing settling of particulate.

3) Rotary stirrers (for example, magnetic stirrers by Cole-Parmer Instrument Company of Niles, Ill. or that described in U.S. Pat. No. 5,834,739 (1998) to Lockwood, et al.) are effective for stirring solutions in mixing chambers having axial symmetry, such as beakers. However, rotary stirrers are not well adapted to use in rectangular reservoirs that receive pipette tips. Centrifugal effects cause a vortex, where the fluid level in the reservoir to vary from low near the stirring element to high near the edges of the reservoir, possibly causing pipettes to draw air. Also, given the differing densities of the components of the mixture, the stirrer may act as a centrifuge, increasing the concentration of denser materials at increasing distances from the stirrer. It may be impractical to locate a continuously rotating stirrer in a standard reservoir without physically interfering with the pipette tips.

4) U.S. Pat. No. 4,477,192 (1984) to Bonney describes a magnetic stirrer in which the stirring element moves erratically within a mixing chamber. If used with pipetting equipment, the stirring element will tend to interfere with the pipette tips, or vice versa.

5) Agitation of the entire reservoir (using, for example, a laboratory platform shaker) may require that the reservoir be mechanically fixed to the agitator, a disadvantage for convenient movement or replacement of the reservoir. The magnitude of the agitation is limited to the point where fluid spills or splashes from the open-topped reservoir, and to the extent where the motion interferes with the operation of pipetting equipment.

6) Agitation may be achieved by imparting motion to the fluid via elastic deformation of some portion of the interior surface of the reservoir. U.S. Pat. No. 4,793,714 (1988) to Gruber discloses a mixer which employs a vibrating membrane on some wall of the mixing chamber. U.S. Pat. No. 4,232,972 (1980) to Levin discloses a mixer here the walls and bottom of the chamber are deformed to impart impulses to the fluid These methods require a purpose-built mixing chamber, which is disadvantageous compared to using simple, disposable, standard reservoirs.

7) U.S. Pat. No. 5,736,100 (1998) to Miyake et al., discloses a method for mixing by imparting ultrasonic waves into the material to be mixed. Unless very carefully directed and controlled, ultrasonic mixing produces highly localized agitation, which may not produce consistent mixture and which may cause splashing and undesired heating.

8) U.S. Pat. No. 5,443,791 (1995) to Cathcart et al. (column 9, line 33 and column 36, line 11) describes a method for stirring using the pipetting device itself. The pipette tips repeatedly aspirate and dispense the fluid in the reservoir and may be moved within the reservoir to achieve mixing. This method requires that the pipettes spend extra time within the reservoir to effect mixing. In addition, the pipette tips may be required to make extra trips to the reservoir to prevent settling even when no sample from that reservoir is immediately needed.

9) HyperTask of Hopkinton, Mass. markets a mixer for use in a reservoir with automated pipetting equipment. In this device, a mixing paddle reciprocates horizontally within the reservoir. This horizontal motion allows pipetting from only one end of the reservoir, preventing the use of a complete array of pipettes.

10) U.S. Pat. No. 5,100,242 (1992) to Latto discloses a mixing method in which an orifice plate is reciprocated within a fluid at right angles to the plane of the plate to generate vortex rings. The disclosure specifies a range of ratios of motion amplitude to orifice diameter. The present invention is not constrained to operate within that range, nor is it constrained to use circular holes. In addition, the disclosure specifies that to generate effective ring vortices, the minimum distance from the center of an orifice to the edge of the orifice plate or to the edge of another orifice is twice the diameter of the orifice. The present invention is not so constrained, and in fact, in the preferred embodiment, the present invention's orifices are doser together than Latto specifies. In short, the present invention is not a ring vortex mixer.

BRIEF SUMMARY OF THE INVENTION

The present invention comprises a horizontal, perforated agitator element and means to cause the agitator element to reciprocate vertically within a reservoir containing a fluid suspension, solution, or mixture. The perforations in the agitator element are sized and located so that an array of pipette tips may be inserted into the fluid through the moving agitator element without interference.

Several objects and advantages of the present invention are:

(a) to provide agitation of fluid mixtures in a reservoir without requiring regular participation or attention from a human operator;

(b) to provide a well controlled, uniform fluid mixture in a reservoir;

(c) to provide continuous agitation in a reservoir without impeding or interfering with the insertion of a complete array of pipettes into the reservoir;

(d) to provide agitation with an agitating element that is simple in configuration and is easy to clean or replace;

(e) to provide agitation with minimal risk of contamination, spillage, or leakage;

(f) to provide agitation in standard reservoirs, maintaining compatibility with typical laboratory equipment;

(g) to provide agitation without requiring the automated pipetting device to spend extra time or make extra trips to the reservoir; and (h) to provide agitation in an open-topped reservoir without splashing or excess sloshing.

Further objects and advantages will become apparent from a consideration of the ensuing description and drawings, and this list is not intended to be conclusive.

Figure 1:
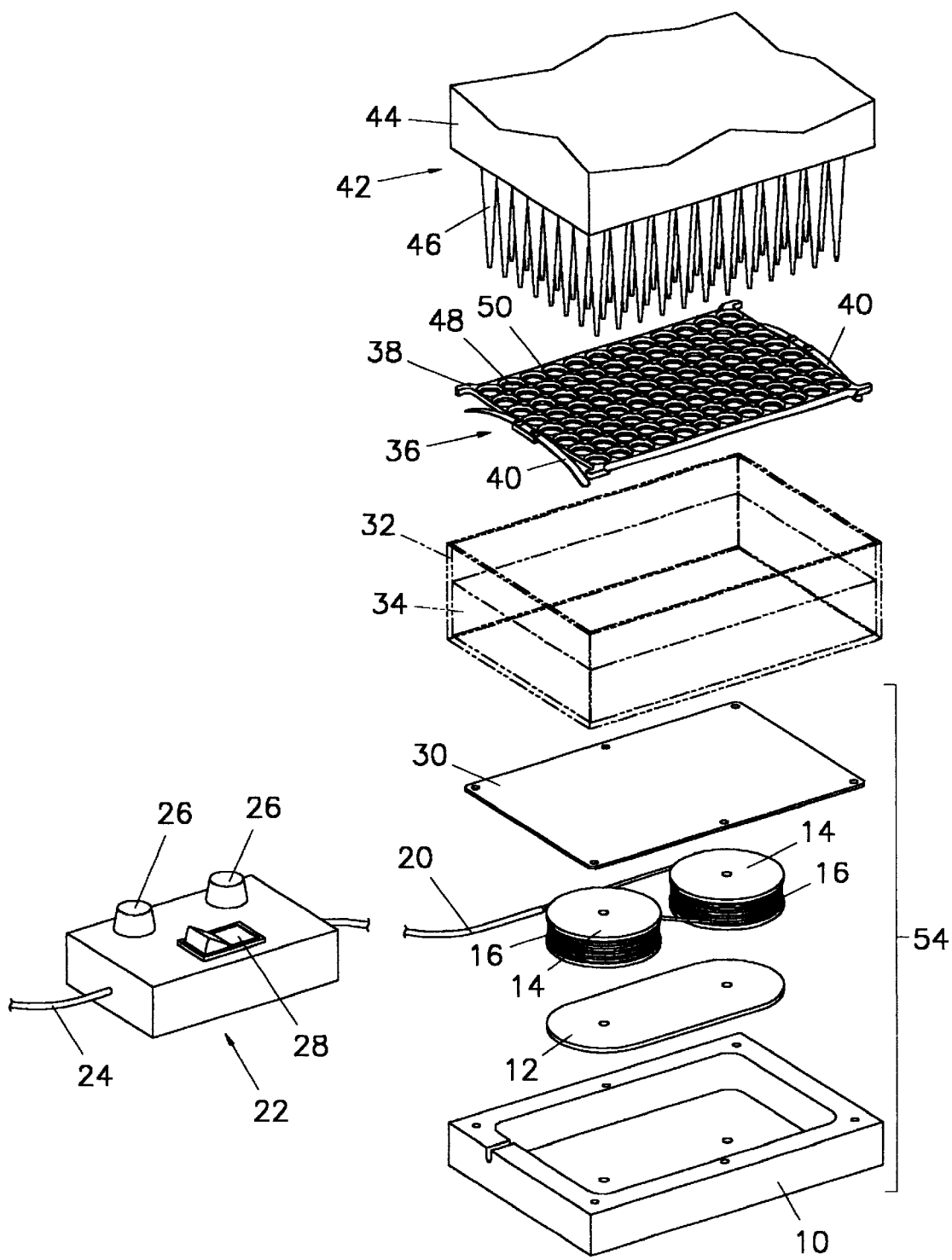
FIG. 1 shows an exploded isometric view of a preferred embodiment of an agitator.

REFERENCE NUMERALS IN DRAWINGS 10 housing
12 base plate
14 spool
16 wire windings
20 electromagnet cable
22 electromagnet driver
24 power cable
26 timing adjustment knobs
28 power switch
30 cover
32 reservoir
34 fluid suspension or mixture
36 agitator assembly
38 agitator plate
40 leaf spring
42 pipette head assembly
44 pipette head
46 pipette tip
48 pipette clearance hole
50 interstitial hole
52 direction of agitator reciprocation
54 agitator base assembly

DETAILED DESCRIPTION OF THE INVENTION

Description of Figures

Figure 2:
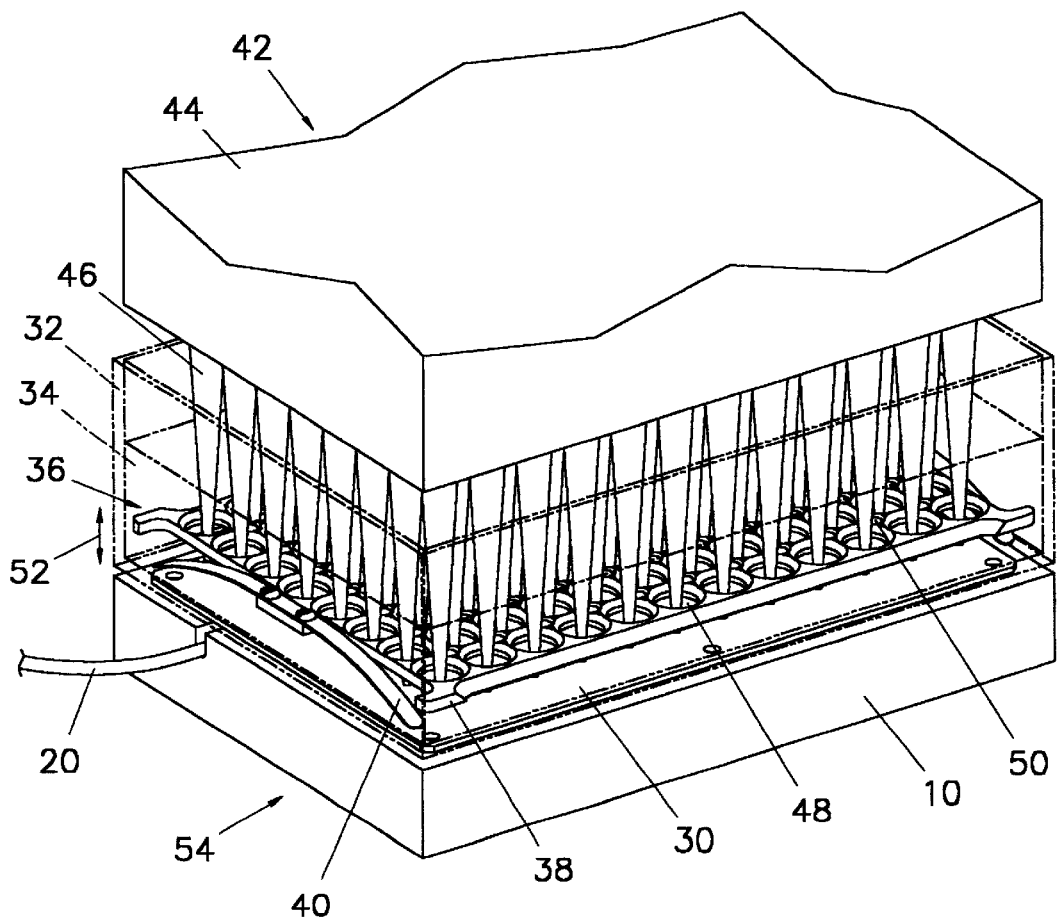
FIG. 2 shows an assembled isometric view of a preferred embodiment of an agitator with pipette tips immersed in the fluid.

A preferred embodiment of the present invention is illustrated in FIG. 1 (exploded view) and FIG. 2 (assembled view). Enamel coated copper wire 16 is wrapped around two spools 14. Spools 14 are made of a magnetically permeable material, low carbon steel in this embodiment. Wire windings 16 are wound around spools 14 in series, clockwise around one spool 14, and counter-clockwise clockwise around the other spool 14. Wire windings 16 terminate in a two conductor insulated cable 20.

Spools 14, wound with wire 16 are fastened to a base plate 12 and a housing 10. Base plate 12 is constructed from low carbon steel, a magnetically permeable material. Aluminum housing 10 contains a cavity to accommodate spools 14, wire windings 16, and base plate 12. Housing 10 also has a feedthrough notch to allow electromagnet cable 20 to exit housing 10. An aluminum cover 30 is fastened to the top of housing 10. Spools 14, wire windings 16, base pate 12, housing 10, and cover 30 comprise agitator base assembly 54.

Electromagnet cable 20 electrically connects agitator base assembly 64 to an electromagnet driver 22. Electromagnet driver 22 contains circuitry that produces an approximately square voltage output, where voltage repeatedly alternates between zero volts and some non-zero voltage, in this case twelve volts. Two timing adjustment knobs 26 control the duration of the zero volt portion of the voltage output and the duration of the non-zero voltage portion of the voltage output. The frequency of the output can be varied between approximately 0.5 hertz and approximately 20 hertz. A power switch 28 turns the device on and off. A power cable 24 connects electromagnet driver 22 to a source of electrical power, not depicted.

A reservoir 32, containing fluid mixture or suspension 34, rests on top of agitator base assembly 54. In this embodiment, reservoir 32 is a standard polyethylene reservoir, commonly used with automated pipetting equipment An agitator plate 38 is constructed from a magnetically permeable material, in this case low carbon steel. The overall length and width of agitator plate 38 are slightly smaller than the interior length and width of reservoir 32. Agitator plate 38 is perforated with pipette clearance holes 48, arranged in an array matching a commonly used standard pipette array in automated pipetting equipment. The diameter of pipette clearance holes 48 is sufficient for clearance during operation. The top edge of each pipette clearance hole 48 is chamfered at forty-five degrees such that the chamfers of orthogonally adjacent holes overlap slightly. Agitator plate 38 is additionally perforated with interstitial holes 50. The top edge of each interstitial hole 50 is chamfered at forty-five degrees so that its chamfer slightly overlaps the chamfers of the surrounding pipette clearance holes 48.

The width of all but the ends of agitator plate 38 is reduced slightly from both long sides. The top edges of the reduced-width portion are chamfered at forty-five degrees over the entire thickness of agitator plate 38. The short sides of agitator plate 38 are indented, leaving a small finger at each corner and a tab on the middle of both short sides of agitator plate 38. Two leaf springs 40 are fastened to the tabs on the middles of the short sides of agitator plate 38 to form agitator assembly 36. Leaf springs 40 are made from stainless spring steel strip, deformed to curve concave downward to form four legs when fastened to agitator plate 38. Agitator assembly 36 is coated in its entirety with a flouropolymer material, PTFE in this embodiment, which is chemically inert with most fluids.

A representation of a pipette head assembly 42 consists of a pipette head 44 and a plurality of pipette tips 46. Pipette head assembly 42 is part of an automated pipetting device, the remainder of which is not depicted.

Description of Operation

Agitator assembly 36 is negatively buoyant in fluid 34, and leaf springs 40 are stiff enough to support agitator assembly 36, so agitator assembly 36 rests on its legs on the bottom of reservoir 32 with the bottom surface of agitator plate 38 elevated above the floor of reservoir 32. The closeness of fit of agitator assembly 36 within reservoir 32 ensures that pipette clearance holes 48 are aligned with pipette tips 46 within some tolerance zone. The size of pipette clearance holes 48 is sufficient to obviate interference between pipette tips 46 and agitator plate 38 within the tolerance zone. Therefore, pipette Ups 46 can be inserted to any depth in fluid 34 from above, aspirate and/or dispense material, and be withdrawn without impedance from agitator assembly 38 and without impeding reciprocation of agitator assembly 38.

When electromagnet driver 22 provides voltage to wire windings 16, current flows through wire windings 16 and magnetic fields are induced. The intensity of these fields is enhanced by the presence of magnetically permeable material within the wire windings 16. Because wire windings 16 are wound on spools 14 in opposite senses, the top of one spool 14 has north magnetic polarity while the top of the other spool 14 has south magnetic polarity. Magnetic field lines tend to arc from the top of one spool 14 to the top of the other spool 14. Base plate 12, of magnetically permeable material, shorts the magnetic field lines from the bottom of one spool 14 to the bottom of the other spool 14, minimizing magnetic field lines from the top of one spool 14 to its own bottom, and increasing magnetic field lines between the tops of spools 14.

The magnetic field exerts an attractive force on agitator plate 38. This downward force deflects leaf springs 40 and moves agitator plate 38 downward through fluid 34. When voltage is cut off from the wire windings 16, the magnetic field dissipates, and deflected leaf springs 40 exert a net upward force on agitator plate 38, causing upward motion of agitator plate 38 through fluid 34. Because electromagnet driver 22 generates voltage alternating overtime between zero and twelve volts, agitator plate 38 is caused to reciprocate vertically through fluid 34. A two-headed arrow 52 illustrates the reciprocating movement of agitator plate 38.

When agitator plate 38 moves through fluid 34, fluid 34 is displaced through perforations 48 and 50 and around edges of agitator plate 38. This displacement causes mixing and prevents settling or agglomeration of the various components of fluid 34. The presence of interstitial holes 50 and the chamfering and profiling of agitator plate 38 minimize flat areas on the top of agitator plate 38. By minimizing flat areas, stagnation on agitator plate 38 is minimized, preventing settling on agitator plate 38 and ensuring effective agitation.

Timing adjustment knobs 26 are used to optimize the agitation action. Optimal settings depend on the nature of the material being agitated, and are determined empirically.

The invention operates continuously, and pipette tips 46 may be inserted and withdrawn at any time to extract well-mixed material, requiring no synchronization between pipetter and agitator.

Description and Operation-Alternative Embodiments

While the above-described embodiment contains many specificities, these should not be construed as limitations on the scope of the invention, but rather as an exemplification of one preferred embodiment thereof.

The force that moves the agitator may be derived in a number of ways. Some alternative methods follow:

Direct mechanical drive, utilizing electric motors, solenoids, pneumatics, hydraulics, and/or any number of other machines.

Electrostatic drive, using charged bodies to repel and/or attract the agitator element.

Alternative magnetic drive configurations, including magnets driving agitator from beside the reservoir or using an agitator element made of permanently magnetic material which may be attracted and/or repulsed.

Any of the above drive configurations can obviate the need for the spring elements on the agitator element by providing drive force in both stroke directions or by using gravity as the return force (for example with repulsive magnetic force from below).

The agitator element has alternate embodiments as well. Some alternative embodiments are listed below:

As stated above, different drive configurations can allow the elimination of the spring elements.

The agitator perforations may be of non-circular form, square for example, and interstitial holes may be enlarged, reduced, added, or eliminated.

The agitator perforations may be configured so that a single perforation provides clearance for more than one pipette tip.

The agitator may be shaped to conform with and operate in reservoirs with non-rectilinear shapes, for example with sloping, curved, or v-shaped floors and walls.

The agitator may be constructed to allow the insertion or presence of items additional to pipette tips into the reservoir, e.g. temperature monitoring equipment, inlet and outlet tubes, reservoir baffles, etc.

Depending upon drive configuration, the agitator may be constructed from alternate materials, such as plastics or other inert materials, which can eliminate the need for coatings.

Agitator and spring elements may be configured to be integral with the reservoir.

The agitator/spring element may be disposable or it may be reusable.

The agitator element may be comprised of two or more separate parts. This configuration is suitable for reservoirs with baffles or dividers.

Spring elements may be eliminated or alternatively embodied in the following ways, among others:

The spring elements may be in any form of spring, including flat springs, coil springs, gas springs, wavy springs, Belleville springs, or numerous other forms.

The spring material may be changed depending on applications, for example to plastic.

The spring function may be part of the agitator itself. That is, the agitator itself may flex so as to provide its own return force.

The spring function may be achieved by making the agitator element positively buoyant in the fluid, so that the return force is the buoyant force.

The overall configuration of the device need not be as described in the preferred embodiment. For example, the reservoir and drive system may be constructed so they are integral to one another. One drive system may be used to drive numerous agitators in numerous reservoirs, or the drive system for a single agitator may be comprised of several drive components.

We claim:

1. A device for agitating fluids, comprising:

(a) an agitator element of substantially lamellar form, disposed substantially horizontally within a fluid inside a container, having holes therein, said holes disposed in an array substantially matching a fixed array of pipette tips and shaped and sized so that said pipette tips may be moved through said holes in said agitator element without said pipette tips and said agitator element physically contacting one another;

(b) means for intermittently moving said agitator element from a first position to a second position in a substantially vertical direction; and (c) means for returning said agitator element from said second position to said first position in a substantially vertical direction.

2. The device claimed in claim 1 wherein said agitator element comprises a magnetic attraction portion and wherein said moving means comprises an electromagnet, said electromagnet intermittently energized to attract said magnetic attraction portion and move said agitator element from said first position to said second position.

3. The device claimed in claim 2 wherein said returning means comprise a biasing means that causes said agitator element to return to said first position when said electromagnet is de-energized.

4. The device claimed in claim 3 wherein said biasing means comprises one or more mechanical springs.

5. The device claimed in claim 3 wherein said agitator element is buoyant within said fluid and said biasing means comprises flotation of said agitator element within said fluid.

6. The device claimed in claim 1 wherein said agitator element comprises a permanent magnet portion and said moving means and said returning means comprise an electromagnet energized by a current which intermittently alternates its direction, thereby alternatively attracting and repulsing said permanent magnet portion and causing said agitator element to reciprocate.

7. The device claimed in claim 1 wherein said moving and returning means comprise a reciprocating machine directly attached to said agitator element.

8. A method for simultaneously agitating and pipetting fluids, comprising:

(a) providing an agitator element of substantially lamellar form, disposed substantially horizontally within a fluid inside a container, having holes therein, said holes disposed in an array substantially matching a fixed array of pipette tips and shaped and sized so that said pipette tips may be moved through said holes in said agitator element without said pipette tips and said agitator element physically contacting one another;

(b) reciprocating said agitator element in a substantially vertical direction;

(c) vertically inserting said pipette tips into said fluid such that said pipette tips and said agitator element do not contact one another;

(d) pipetting into and/or out of said fluid using said pipette tips; and (e) vertically withdrawing said pipette tips from said fluid.

* * * * *